(12) United States Patent
Cullimore

(10) Patent No.: US 9,856,504 B2
(45) Date of Patent: Jan. 2, 2018

(54) INTERACTIVE DEVICE FOR THE MICROBIOLOGICAL DETERMINATION OF ACTIVITIES BETWEEN NEIGHBORING COMMUNITIES WITHIN PREPARED NATURAL SAMPLES

(71) Applicant: D. Roy Cullimore, Regina (CA)

(72) Inventor: D. Roy Cullimore, Regina (CA)

( * ) Notice: Subject to any disclaimer, the term of this patent is extended or adjusted under 35 U.S.C. 154(b) by 551 days.

(21) Appl. No.: 14/467,446

(22) Filed: Aug. 25, 2014

(65) Prior Publication Data

US 2016/0053294 A1 Feb. 25, 2016

(51) Int. Cl.
*C12M 1/34* (2006.01)
*C12Q 1/04* (2006.01)
*G01N 21/77* (2006.01)

(52) U.S. Cl.
CPC ....... *C12Q 1/04* (2013.01); *G01N 2021/7759* (2013.01); *G01N 2021/7766* (2013.01)

(58) Field of Classification Search
CPC ............. C12Q 1/04; G01N 2021/7766; G01N 2021/7759
See application file for complete search history.

(56) References Cited

U.S. PATENT DOCUMENTS 5,139,685 A * 8/1992 de Castro .......... B01D 39/2017
 210/435
5,187,072 A 2/1993 Cullimore et al.
D687,512 S 8/2013 Cullimore

FOREIGN PATENT DOCUMENTS

DE 3929751 A1 * 3/1991 ......... G01N 21/8483

* cited by examiner

*Primary Examiner* — William H Beisner
(74) *Attorney, Agent, or Firm* — Walter A. Rodgers

(57) ABSTRACT

A device for the microbiological detection and analysis of a controlled interface where known and controlled exposure of a sample of interest interacts with one of series of porous reactive zones in a manner that allows discernable activity to be detected. A favorable environment within the device allows agents emanating from the sample of interest to react with specific agents emanating from the porous reaction zone in a manner that is repeatable and precise.

3 Claims, 6 Drawing Sheets

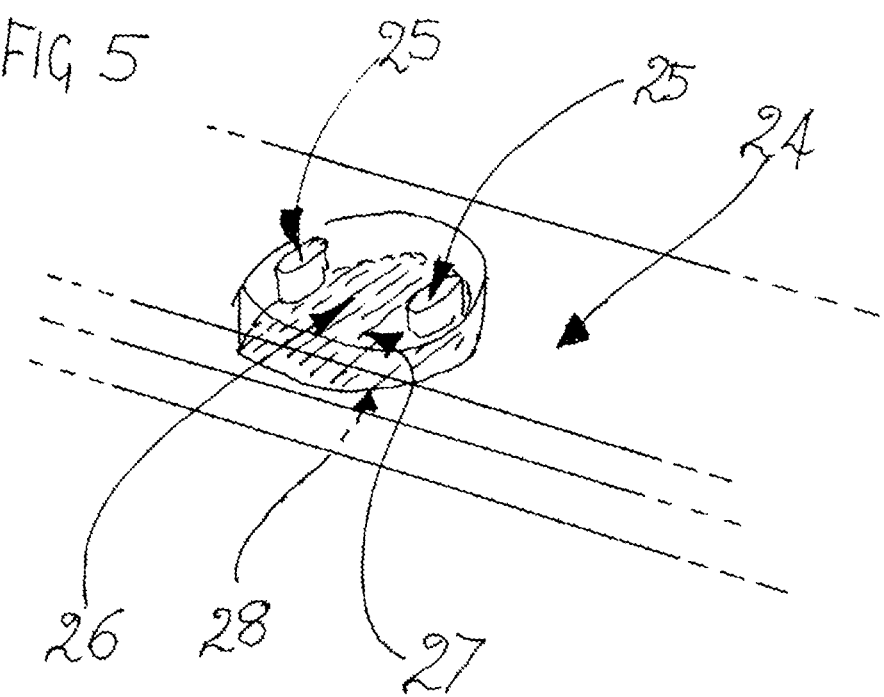

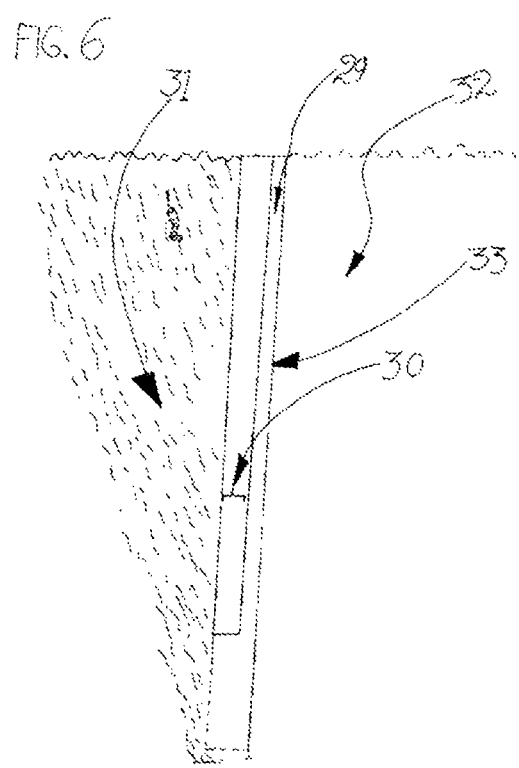

INTERACTIVE DEVICE FOR THE MICROBIOLOGICAL DETERMINATION OF ACTIVITIES BETWEEN NEIGHBORING COMMUNITIES WITHIN PREPARED NATURAL SAMPLES

BACKGROUND OF THE INVENTION

The present invention relates to the microbiological analysis of a natural sample originating in a porous, fractured or liquid material which is prepared in a manner for the qualitative and/or quantitative determination of viable communities of interest. The deployment of the device to intimately interact with the sample of interest is specifically designed to detect active communities of bacteria within the sample being investigated and by means of intrinsic or extrinsic changes associated with the device to evaluate their activities.

The preparation of the samples from qualitative and semiquantitative soil with fertility assay using intrinsic or cultured soil algae is known from British patent No. 1405/62. This method places a series of porous cellulosic discs pretreated to differentiate the status of nitrogen, phosphorus and potassium within the underpinning soil sample.

In the development of this invention, regarding the deployment of porous discs, it became apparent that further improvements could be made to the device and the structure and form of the porous structure with defined modifications to the manipulated environment within the device. Further improvements were achieved in the modification of environment developed within the device by the application of specific chemistries (U.S. Pat. No. 5,187,072) and with the introduction an oxidation restriction achieved in the form of a floating impermeable device. This device was further modified (U.S. Pat. No. D687,512) by increasing the surface areal contact points to increase the microbiological attachment potentials to the floating device. An additional device was developed to increase the surface area created by the deployment of a porous structure to release selected chemicals into the contained sample within the device positioned by a peninsulate extension. It became evident during development of the invention that that a number of unique features could be incorporated into the device. This invention relates to the more convenient assessment to the activities of microorganisms extrinsic to the device but still within the zone of intimate interaction with diagnosable outcomes.

BRIEF SUMMARY OF THE INVENTION

According to this invention, there is a porous structure that is positioned in intimate contact with the extrinsic environment in a manner that facilitates the detection of events that have diagnosable value. The device is placed in a manner that would allow intimate contact at those points considered to be able to trigger such diagnoses such as products between the extrinsic sample environment and the agents contained within the device. The device, therefore, primarily creates designed interactions between the device and the environment being sampled whereby defined signals define a positive detection. This component forms a unique microbiological platform for the detection of signals unique to biological activities associable with significantly important reaction events and times within the investigative process.

To ensure the correct positioning of the microbiologically interactive platform there has to be a positioning of the device within the environment being sampled. While the prime objective is the positioning of the reactive components on the device, it is also important to assure that intimate and potentially reactive site within the environment are explored. Hence, the device may assume any positioning that would allow the signals or events implicit in a positive detection to be recognized.

There are two additions relating to positioning and interaction that allow the device to interact with some parts of the localized sample of interest. These additions are formed by the interfacing components that are established within or upon the reactive sites of the device. This assures a consistent and interactive relationship between the active sites on the device and the targeted sites on the sample of interest. Such precise positioning of the reactant site with the sample site does not dictate a positioning of the device relative to gravity but rather as a convenience to the determination of the function or component of interest within said sample. Precise positioning relates to assuring that there is an intimate contact between active sites on the device and the sample of interest when being evaluated.

This device, by means of the microbiological and chemical interactions, creates a potential for identifiable reactions between the reactive sites inherent in the device and the interfacing sites within the sample of interest. These interactions are controlled by the rapid positioning of the of the reactive sites on the device on to the sample site of interest and allowing the saturation of the interactive sites with a solvent such as water in order to ensure a conformed nature to the significant interactions. Reactive sites, when positioned in an interactive and solvent saturated manner, release by diffusion and solubilization the entrenched agents from the site and into the sample of interest. Concurrently agents are released by the nature of the saturating applied solvent and may react in identifiable manners with the agents originating from the reactive sites of the device. Agents may be defined for the purpose of this invention as physicochemical factors or related to the intrinsic microbiological communities. Interactions are defined as being significant as identifiable events that are recognized between agents being released from the reactive sites of the invention and agents being released from the sample of interest.

In the preparation of the reactive site, according to this invention, the site may include both porous and nonporous structures layered in a manner that would allow containment of the applied diagnostic agents without significant deterioration of quality during storage. Layering of these structures is designed to further reduce the potential for deterioration caused by the various agents becoming subjected to casual storage influenced interactions. For the apparati in accordance with this invention, the reactive sites are formed as one or more layered structures that include a porous structure to contain such agents, overpinning porous structure that might be pigmented in a manner that would allow colorimetric reactions to become readily recognizable, and nonporous layers that would either contain significant chemicals or provide protection for the reactive layers at the reaction site. In the event that this nonporous layer performs a protective function, it can be removed prior to the assay of the sample if it is the last layer applied to the reactive site. In essence, the functionally essential component is the layers within the primary site at which identifiable diagnostic events are generated through the interaction between the agents associated with the porous layers and agents within the local environment of the sample being tested which jointly causate the interaction of significance. The prime designed event is the interaction of agents from the porous layers with agents associated with the sample in such a manner that a diagnosable product is achieved.

Additionally, the positioning of the device, carrying one or more porous reactive zones, becomes critical to the administration of the invention. This positioning of the reactive porous zone and the sample thereunder affects the outcome of the test. In practice, lateral arrangements with reaction zone down interfacing with the sample enquiry zone appears feasible for water samples, whereas in soil samples the arrangement would preferably be vertical. For soils there is automatically a natural porosity in the soil that would restrict the zone of reaction. For water there is commonly a hydraulic fluidity that significantly embraces any restrictions in the zone of reaction. In the latter event, the water sample of interest is confined by a structure that would limit the hydraulic fluidity and effectively confine at least partially that volume of water sample that would then be the subject of the investigation.

Common and unique features of the interactive events are as a result of the close proximity of the layered materials containing the applied diagnostic reactants to the investigated sample, the nature of the water arising from the sample and upon some occasions applied water, the form of reactions originating from the applied agents within the layered device and the natural agents present in the natural sample. Significant products of such reactions between the applied and natural agents when detection occurs would be a clear signal such as colorimetric that would then be recognized as detected.

Preferred features for the device relate to the use of a porous layered device which for analytical purposes allows the convenient recognition of a positive detection where that agent is present within the natural sample being investigated. This invention primarily relates to the form of the porous layered structure that includes the reactants necessary for the completion of the determinative functions in the analysis of a suitably prepared natural sample emplaced by the porous layered structure containing the reactants. The shape of the layered porous structure is dictated in part by the purpose of the devices analytical function. For soil samples, the device carrying one or more of the porous layered structures is placed directly in a vertical manner in the soil thus allowing analytical functions to detect the presence or absence of the agent of interest. For water samples, the porous layered structures are exposed within a partially retained water sample so that the errors associable with hydraulic flows are controlled significantly.

BRIEF DESCRIPTION OF THE SEVERAL VIEWS OF THE DRAWINGS

The features and advantages of the invention will appear from the following description with reference to the accompanying drawings of which:

FIG. 5 is a view from a 45 degree angle above the assembled and charged device as defined in FIGS. 1 through 4 illustrating the most likely sites for diagnosable reactions.

FIG. 6 illustrates a rectangular porous reaction zone in intimate contact with a soil sample wherein the reaction site would be at the interfaces between the porous reaction zones of the invention and water contained within the soil samples matrix.

DETAILED DESCRIPTION OF THE INVENTION

This device is designed to be used by placement of the liquid or semisolid porous sample of interest in close association with the porous reactive zones placed within the device. For such samples, there has to be interaction with the porous reactive zone of the device under localized water saturated conditions. Interaction of the porous reactive zone with the sample to be tested involves reaction products that are generated in an observable manner in such cases as positive detection of the daughter product. Detection, therefore, involves a generated event that may be physical, chemical or biological of the positivity declaring agent associable with, but not necessarily generated on, the porous reactive zone. This invention directly relates to the occurrences of positive detection within the sample as a direct or indirect reaction with components within specific porous reactive zones. Techniques developed around this device center upon the porous reactive zone that interacts with the sample of interest in the presence of liquid water. This invention, therefore, relates primarily to the manner in which layers of porous materials containing different but essential reacting agents will upon dissolving and interacting with agents emanating in the sample cause definable reactions where a positive detection is determined.

The analytical procedures, according to this invention, relate to the forms of any interaction between agents present in the sample being tested and agents emanating from the porous reactive zone that is an integral part of the invention. Critical to this invention is the porous reactive zone that may contain up to three separate chemical and/or biological agents as three layers arranged as three stratified zones with the upper porous layer interacting directly with the sample. For the middle and lower porous layers, these may include specific diagnostic agents that together or separately will interact with each other and agents within the sample of interest causing potential means to recognize particular agents or daughter products.

Figure 1:
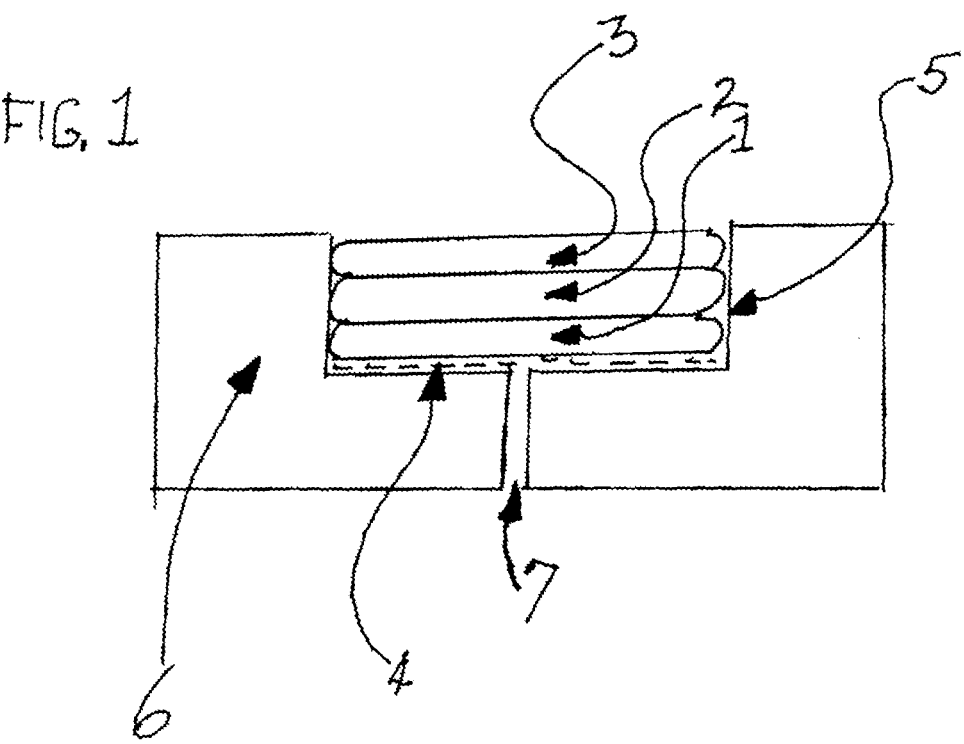
FIG. 1 is a sectional viewing the essential features of the device, according to this invention.

Critical are the analytical roles that are affected by the structure of the porous reactive zones that contain up to four layers, as illustrated in FIG. 1. Essentially these reaction zone layers include the lowermost layer 1 which has a porosity to match the requirement of the primary reactant. Set directly above layer 1 is a second central porous layer 2 that includes the secondary reactant. The uppermost porous layer 3 has a diagnostic purpose since the diffusive movement of reactants in layers or discs 1 and 2 and into 3 causes such interactions with water from the sample of interest once the layers 1, 2 and 3 become exposed to that sample. Beneath the three porous layers forming the reactant zone, there is an evaporated film 4 on the floor of cavity 5. Evaporated deposit 4 allows the necessary buffering of the pH into a suitable range for the effective use of the reactants presented in the lower layer 1 and central layer 2. Cavity 5 containing layers 1, 2 and 3 and deposit 4 has tight-fitting vertical walls to ensure containment and is surrounded on three sides by the nonporous supporting structure 6.

In order to allow the effective wetting and or saturation with water associated with the sample of interest, conduit or tube 7 passes from the cavity through the bottom of supporting structure 6 to allow the venting of air and unrestricted entry of the water sample. The geometric shape of cavity 5 varies with the precise analytical function for the device and commonly is circular or rectangular depending upon whether a specific or generalized analytical function is required.

Figure 2:
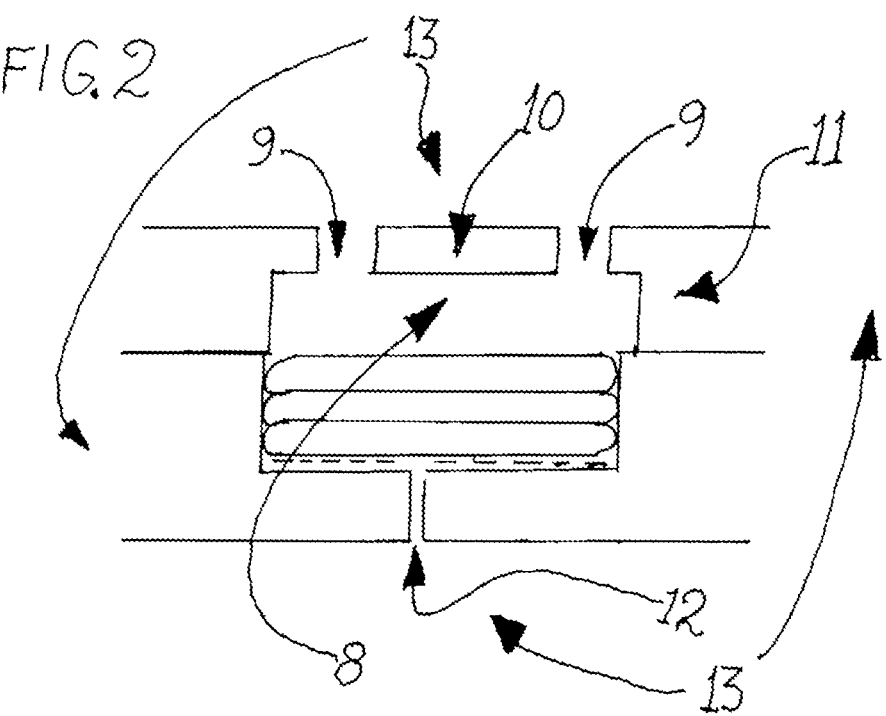
FIG. 2 is a similar section to that shown in FIG. 1 except that the cap is incorporated into the invention.

For conditions where a water sample is to be analyzed, FIG. 2 illustrates the capping that is applied to ensure that a part of the water sample becomes entrained over the porous reaction zone 8. This sample enters through sample ports 9 formed in roof 10 of cap 11. Such a procedure is enacted by the inversion of the device which is then lowered in the liquid sample of interest. As the sample enters through the sampling ports 9, air from the porous zone cavity is forced out through the vent conduit or tube 12. To achieve this sampling procedure, the capped device needs to be lowered into the liquid sample 13 which saturates the voids within the cavity with water while allowing the air to escape through inverted vent tube 12.

Figure 3:
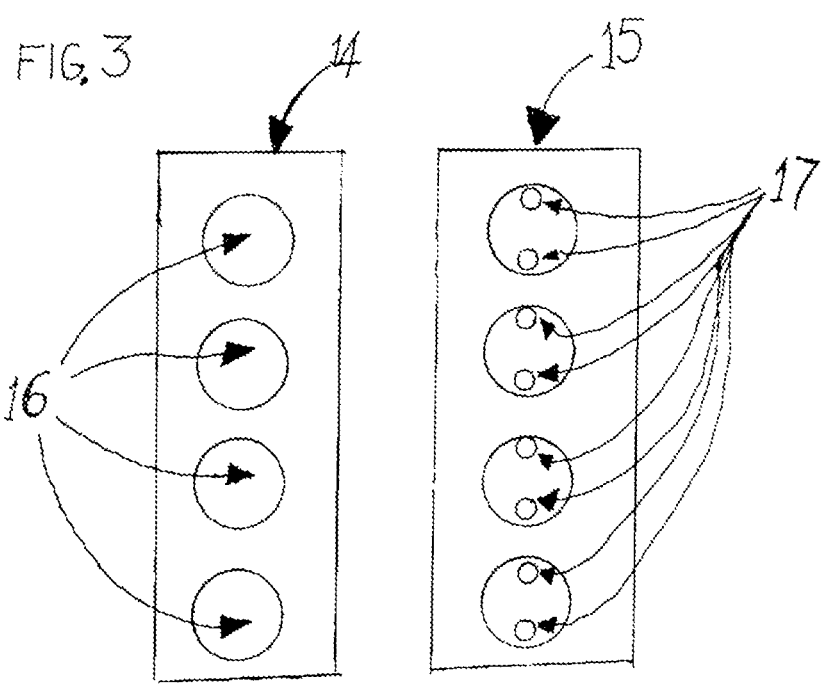
FIG. 3 is a view from above onto the unassembled device as shown in FIG. 1 and the cap shown in FIG. 2.

Positioning the bottom structure shown in FIG. 1 with porous reactive zones illustrated in FIG. 2 results in the four-zoned device as shown in FIG. 3. Here the base of the device 14 contains four circular porous reaction zones 16 while top structure 15, which fits onto base 14, allows two potential entrance points 17 for each cavity to enable filling the device with the liquid sample of interest by inversion of the device into the liquid sample.

Figure 4:
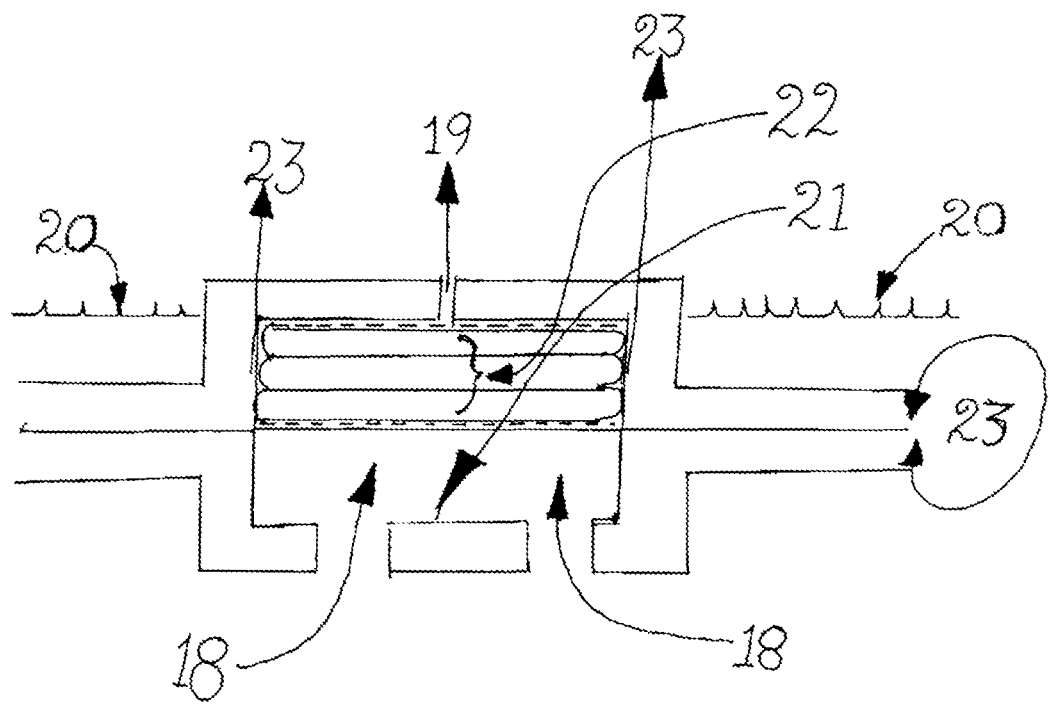
FIG. 4 is a side sectional view of the assembled device in which water sample enters into the device to initiate the generation of significant reactions.

Inversion of the device just below the water level is illustrated in FIG. 4. Here the water forming the sample of interest enters ports 18 while at the same time water is evacuated through vent 19 now on the top of the inverted device close to the liquid level 20 from which the sample is obtained primarily to collect within the cavity 21. Once the cavity is filled, the liquid sample moves up through the reactant discs 22 replacing the air with the sampled liquid. Once the sampling is completed, the device is again fully reinverted as shown by the numeral 23 so that the reactions can be observed.

FIG. 5 illustrates the manner in which a single circular reaction cavity is utilized in order to observe a significant recognized positive detection. Here the device is inverted as indicated by the numeral 24 so that sampling ports 25 are positioned uppermost. Reactions may occur within the contained positively active sample as a determinable event occurring above the porous reaction zone 26 or on the uppermost porous reaction disc 27. In the event of the positive detection involving the bottom or the central porous interactive layer, the product reaction may be more effectively viewed by turning the device over as indicated by the numeral 28.

In the event the uppermost porous reaction disc is used to determine the presence of an agent within a porous soil matrix, then the device is placed vertically adjacent the matrix to assure intimate contact. This use is shown FIG. 6 as a vertical soil profile wherein device 29 has a rectangular porous reaction zone 30 which consists of three distinct porous layers with the uppermost porous layer interacting with soil matrix 31. While FIG. 6 shows an interfacial interaction between the porous reaction zones directly with the soil sample matrix, there remains the possibility to leave the other side of the device uncovered, as indicated by the numeral 32, thus allowing direct observation of possible reactions through the visible side 33 of the exposed device. In this event, the device is forced into the sample matrix being analyzed and the initial profile of the device below the rectangular porous reaction zone is shaped in a cone or a point that would then allow reduced resistance to the injection of the device into the matrix.

NUMERAL GLOSSARY

FIG. 1
1. Lower porous layer supporting selected reactants
2. Central interactive porous layer
3. Upper porous layer defining potential reactant products
4. Dried layer of selected reactants
5. Reactant cavity defined in shape by tightly fitting around the selected porous layers
6. Supporting structure
7. Process vent to allow sample egress into porous layers FIG. 2
8. Cavity in the top plate aligned to the reactant cavity in the base plate
9. Sampling ports that allow the unrestricted entry of the liquid sample into the restricted cavity
10. Lid section made of a transparent material that allows the diagnostic reactions to be see on or within the restricted cavity
11. Capping device that fits tightly over the reactant cavity in a manner that allows the contained liquid sample to be confined
12. Process vent
13. Bulk liquid from which the sample is confined above and within the porous layers restrained within the cavity FIG. 3
14. Reactant cavity base support structure viewed from above
15. Sampling lid upper support structure viewed from above
16. Reactant cavities within the base support structure viewed from above
17. Position of sampling ports in the upper support structure above the porous structures present in the base support structure FIG. 4
18. Device placed in water sample with the porous reactant discs positioned above the upper plate causing the water sample to enter through the inverted upper plate and fill the cavity and saturate the porous discs within the cavity
19. As the water sample enters then the air within the cavity moves upwards to escape through the vent
20. Liquid sample: air interface into which the device is lowered laterally upside down to allow liquid sample to enter the cavity and the porous discs containing reactants
21. Sample liquid fills the cavity
22. Liquid sample saturates the porous discs and sets up conditions agent to reactant reactions
23. Once charged with the liquid sample, the device is removed from the liquid being sampled FIG. 5
24. After sampling using the laterally inverted device, it is inverted again so the sampling ports are upper most on the device
25. Sampling ports now provide exchange points between the atmosphere and the contained liquid sample that remains oxidative when oxygen has permeated into the liquid sample
26. Reaction cavity remains full with the liquid sample and this now becomes a focal region for the recognition of significant reactions and activities of interest
27. Reactions may also occur between the reactants within or around the stacked porous discs and the permeating liquid sample of interest 28. Reactions may be recognized through changes observed on the underside of the base of the device

FIG. 6

29. Device is illustrated without the capping (upper) structure for use on water-saturated porous natural materials whereby there is a direct interface between the reactant porous material and the sampled material such as a soil or a mud
30. Layered porous discs are presented as rectangular layers that interact directly with the porous natural materials to potentially trigger significant reactions
31. Porous natural material such as soil now interfaces directly with the reactant strips to allow the recognition of zones of interaction where the agent of interest is detected
32. Optional interfacing of the porous natural material with the vertical insertion of the device to allow the observation of zonation within a selected interaction between the agent in the sample and reactants associated with the porous zones of the device
33. Geometric shaping of the device to allow a minimum of resistance to movement as the device is moved into position within the porous medium of interest that allows reactions to be observed immediately or after the device is removed from the site of sampling

The invention claimed is:

1. A device lot the detection of microorganisms comprising a support structure,
    a liquid sample having a level,
    said support structure disposed at least partially below said level,
    said structure having first and second portions,
    said first portion comprising a vent extending upwardly above said level,
    said second portion comprising at least one pen extending downwardly below said level,
    multiple porous reactant discs disposed in said support structure,
    at least two of sad porous reactant discs containing differing reacting agents, and
    a cavity disposed in said support structure between said at least one port and said multiple porous reactant discs to receive said liquid sample.
2. The device according to claim 1 wherein said cavity is circular.
3. The device according to claim 1 wherein the outer peripheries of said multiple porous reactant discs are disposed in abutting relation with said support structure.

* * * * *